United States Patent [19]
Johnson et al.

[11] Patent Number: 6,133,045
[45] Date of Patent: Oct. 17, 2000

[54] AUTOMATED SAMPLE TREATMENT SYSTEM: APPARATUS AND METHOD

[75] Inventors: James E. Johnson, Incline Village; James M. Salika; Chih-Chung Chen, both of Reno, all of Nev.

[73] Assignee: Hamilton Company, Reno, Nev.

[21] Appl. No.: 09/032,353

[22] Filed: Feb. 27, 1998

[51] Int. Cl.[7] .............................. G01N 1/14; G01N 35/02
[52] U.S. Cl. ........................... 436/177; 436/180; 436/47; 436/49; 422/63; 422/65; 422/81; 422/100; 422/101; 422/104; 210/406
[58] Field of Search ............................... 436/43, 54, 174, 436/177, 178, 47, 180, 49; 422/100, 63, 101, 65, 104, 81; 210/406

[56] References Cited

U.S. PATENT DOCUMENTS

| | | |
|---|---|---|
| 4,113,434 | 9/1978 | Tanaka et al. . |
| 4,184,961 | 1/1980 | Rynde et al. . |
| 4,766,082 | 8/1988 | Marteau D'Autry .................... 436/178 |
| 4,771,642 | 9/1988 | Parth et al. . |
| 4,810,471 | 3/1989 | Wachob et al. ........................ 422/103 |
| 4,846,970 | 7/1989 | Bertelsen et al. . |
| 4,869,116 | 9/1989 | Meyrat et al. . |
| 4,895,706 | 1/1990 | Root et al. .............................. 422/102 |
| 4,927,604 | 5/1990 | Mathus et al. . |
| 4,948,564 | 8/1990 | Root et al. . |
| 4,952,518 | 8/1990 | Johnson et al. . |
| 4,976,926 | 12/1990 | Matkovich . |
| 5,141,719 | 8/1992 | Fernwood et al. . |
| 5,190,666 | 3/1993 | Bisconte ................................. 210/744 |
| 5,217,619 | 6/1993 | Redmond, Jr. et al. . |
| 5,219,528 | 6/1993 | Clark . |
| 5,227,137 | 7/1993 | Monti et al. . |
| 5,232,666 | 8/1993 | Longman et al. . |
| 5,260,028 | 11/1993 | Astle . |
| 5,273,718 | 12/1993 | Skold et al. ............................ 422/101 |
| 5,283,039 | 2/1994 | Aysta ...................................... 422/104 |
| 5,372,037 | 12/1994 | Butt . |
| 5,380,437 | 1/1995 | Bertoncini ............................ 210/416.1 |
| 5,401,637 | 3/1995 | Pocock . |
| 5,415,051 | 5/1995 | Rokugawa et al. . |
| 5,424,038 | 6/1995 | Benz et al. . |
| 5,490,971 | 2/1996 | Gifford et al. . |
| 5,529,694 | 6/1996 | Strickler . |
| 5,620,894 | 4/1997 | Barger et al. . |
| 5,624,815 | 4/1997 | Grant et al. ............................... 435/30 |
| 5,645,723 | 7/1997 | Fujishiro et al. . |
| 5,660,792 | 8/1997 | Koike . |
| 5,770,157 | 6/1998 | Cargill et al. ............................. 422/99 |
| 5,888,830 | 3/1999 | Mohan et al. .......................... 436/174 |

*Primary Examiner*—Long V. Le
*Attorney, Agent, or Firm*—Bernhard Kreten

[57] ABSTRACT

A sample treatment system for automated extraction of compounds is disclosed. The system includes a housing defining an enclosure including a top cover having an open ended well for allowing a sample plate to nest therein, a automated shuttle means for lateral transportation and vertical lifting of both a waste and a collection plate to selectively address an area below the sample plate for the through passage of fluid from the sample plate and a digitally controlled variable speed vacuum pump operatively coupled to said housing for evacuating air from the enclosure to a degree below atmospheric pressure for through passage of fluid from the sample plate to either the waste plate or collection plate. The shuttle means includes motor drives and positive position feedback for precisely laterally and vertically positioning both the waste and collection plates.

25 Claims, 12 Drawing Sheets

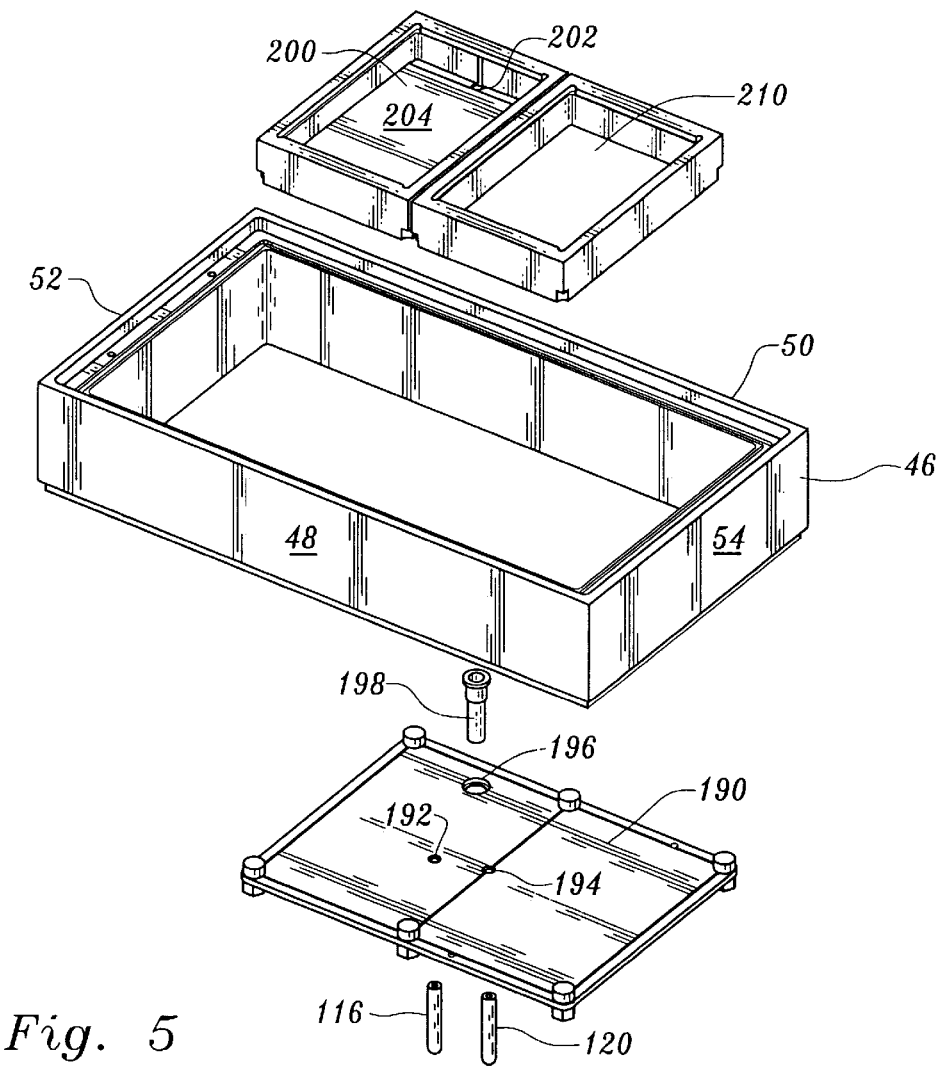
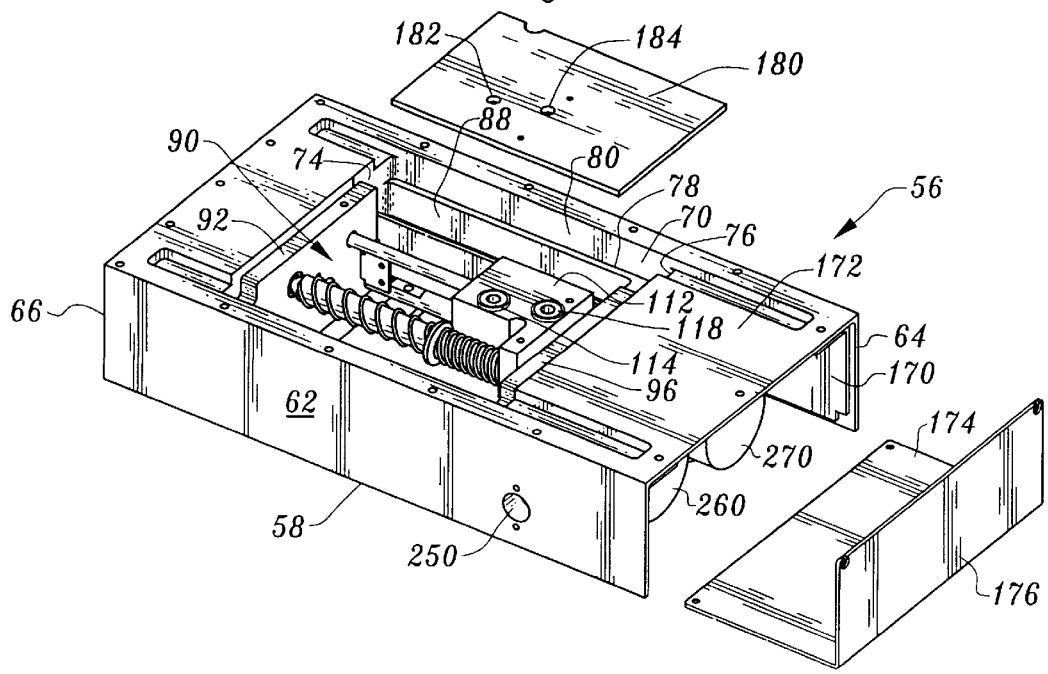
Fig. 5

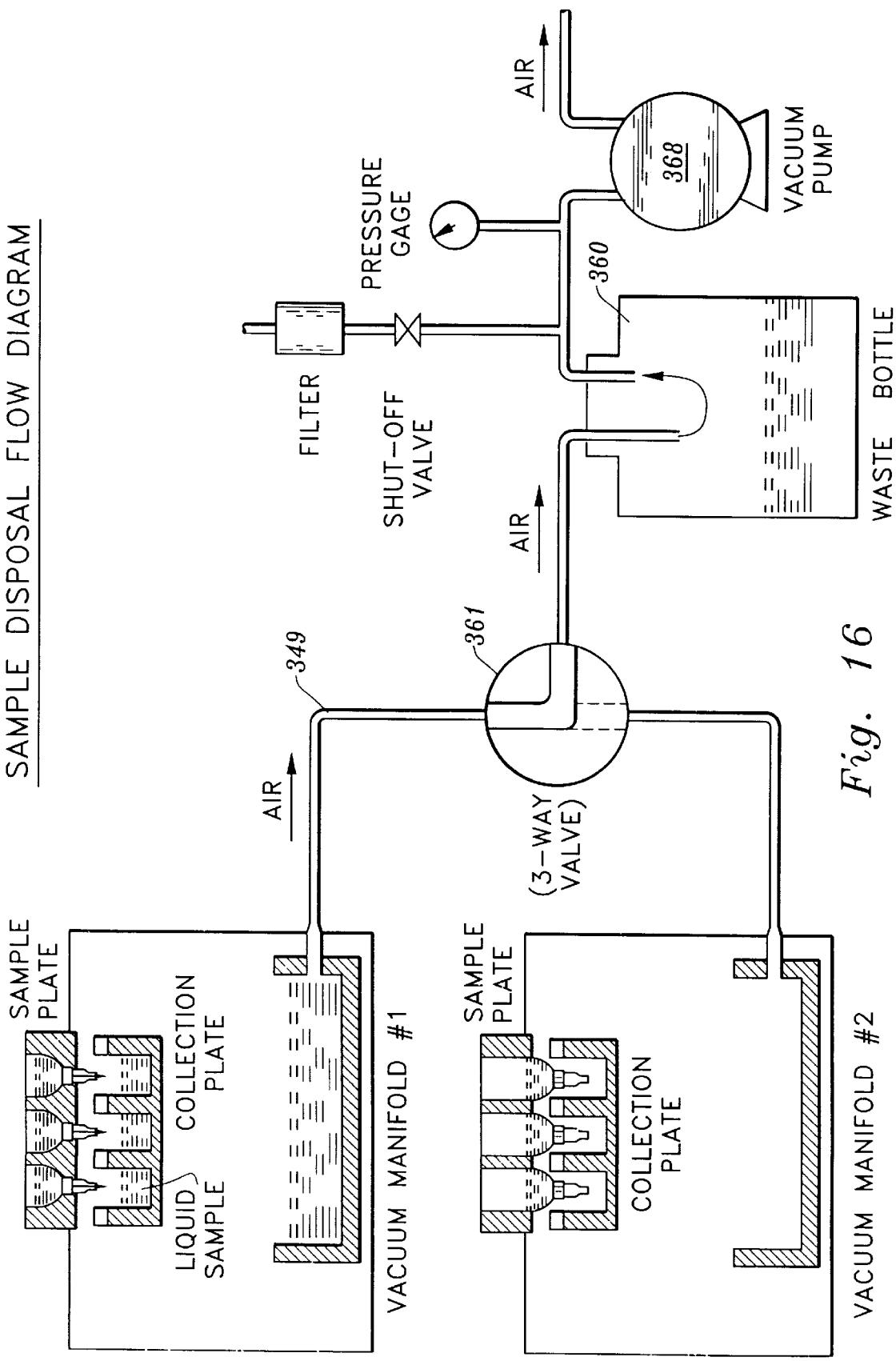

AUTOMATED SAMPLE TREATMENT SYSTEM: APPARATUS AND METHOD

FIELD OF THE INVENTION

The instant invention relates generally to a sample treatment system and, in particular, to a variable controlled vacuum extraction system including a vacuum manifold with both waste and collection sites and a digitally controlled variable speed vacuum pump.

BACKGROUND OF THE INVENTION

Sample preparations in the pharmaceutical industries, chemical industries as well people doing DNA work require many precise liquid handling steps, such as: transfer of samples, dilutions, additions of reagents, transfer of reaction mixtures, etc. Automated liquid handling systems have been developed and are commercially available in the form of programmable pipetting work stations. These automated systems reduce the manual labor involved in the liquid handling and processing of samples.

However, these systems are not completely automatic and still require manual manipulation and user intervention. For example, when using a manual vacuum manifold system with the pipetting work station, the processing of liquids requires human intervention and manual manipulation. Typically, the user is required to place a filter plate on top of the manual vacuum box and then the filter plate is filled with a plurality of samples. Once the filter plate is filled with samples, the user has to manually manipulate the vacuum during the wash steps of the extraction process. Once the wash step of the extraction process is completed, the user carefully removes the filter plate containing the remaining constituents which are being collected. The user then places a collection plate into the vacuum box and then places the filter plate on top of the collection plate and then manually manipulates the vacuum to extract the constituent of interest. Thus, the user is constantly interacting with the system during the collection of samples.

Thus, existing systems have short comings that limit there usefulness, for example, some analytical laboratories process hundreds of samples using solid phase extraction or other techniques. Since the steps are highly repetitive, automated systems are needed to reduce the manual labor involved in the liquid handling and processing steps. In addition, user intervention and manual operations reduce the efficiency of an otherwise automated analytical system.

Therefore, there is a need for an apparatus and method for performing analytical procedures without the need for operator intervention and minimizing the manual tasks before, during and after the analytical procedures.

In addition, there is a need for an apparatus and method which provides automated vacuum control to enhance flow rates through the sorbing media or frit, thus, providing good recoveries and throughput of flow rate dependent compounds. In addition, a system having an automated variable vacuum control would mitigate well to well cross talk tendencies.

The following prior art reflects the state of the art of which applicant is aware and is included herewith to discharge applicant's acknowledged duty to disclose relevant prior art. It is stipulated, however, that none of these references teach singly nor render obvious when considered in any conceivable combination the nexus of the instant invention as disclosed in greater detail hereinafter and as particularly claimed.

| PATENT NO. | ISSUE DATE | INVENTOR |
| --- | --- | --- |
| 4,113,434 | September 12, 1978 | Tanaka, et al. |
| 4,184,961 | January 22, 1980 | Rynde, et al. |
| 4,771,642 | September 20, 1988 | Parth, et al. |
| 4,810,471 | March 7, 1989 | Wachob, et al. |
| 4,846,970 | July 11, 1989 | Bertelsen, et al. |
| 4,869,116 | September 26, 1989 | Meyrat, et al. |
| 4,895,706 | January 23, 1990 | Root, et al. |
| 4,927,604 | May 22, 1990 | Mathus, et al. |
| 4,948,564 | August 14, 1990 | Root, et al. |
| 4,976,926 | December 11, 1990 | Matkovich |
| 5,141,719 | August 25, 1992 | Fernwood, et al. |
| 5,217,619 | June 8, 1993 | Redmond, Jr., et al. |
| 5,219,528 | June 15, 1993 | Clark |
| 5,227,137 | July 13, 1993 | Monti, et al. |
| 5,232,666 | August 3, 1993 | Longman, et al. |
| 5,260,028 | November 9, 1993 | Astle |
| 5,372,037 | December 13, 1994 | Butt |
| 5,401,637 | March 28, 1995 | Pocock |
| 5,415,051 | May 16, 1995 | Rokugawa, et al. |
| 5,424,038 | June 13, 1995 | Benz, et al. |
| 5,490,971 | February 13, 1996 | Gifford, et al. |
| 5,529,694 | June 25, 1996 | Strickler |
| 5,620,894 | April 15, 1997 | Barger, et al. |
| 5,645,723 | July 8, 1997 | Fujishiro, et al. |
| 5,660,792 | August 26, 1997 | Koike |

SUMMARY OF THE INVENTION

The instant invention is distinguished over the known prior art in a multiplicity of ways. For one thing, the instant invention provides an automated sample treatment system for automated extraction of genomic and plasmid DNA or simultaneous solid phase extraction of compounds. In addition, the sample treatment system includes control means to allow integration with an automated pipetting work station. Furthermore, the instant invention includes a vacuum manifold apparatus including an automated shuttle means for lateral transportation and vertical lifting of both waste and collection sites. The shuttle means includes stepper motor drives, positive position feedback and a motor control means. Moreover, the instant invention provides a vacuum control apparatus including a digitally controlled variable speed vacuum pump to automatically control the amount of vacuum being delivered to the vacuum manifold apparatus for providing, inter alia, superior recovery and throughput of flow rate dependent compounds. The instant invention also provides an automated sample treatment system without using complex linkage which can, inter alia, break and/or bind in operation.

In a preferred form, the sample treatment system of the instant invention is integrated with the liquid handling capabilities of a programmable pipetting work station. The sample treatment system includes a vacuum manifold apparatus having a shuttle mechanism, a vacuum control apparatus and an electronic control system.

The vacuum manifold apparatus includes a housing defining an enclosure having a chamber and an upper removable top cover. The top cover includes a centralized open-ended well for allowing a sample plate to nest therein. The chamber includes a substantially planar bottom surface having an outer periphery with upwardly extending side walls formed with the periphery thereby defining an opened top box structure. The chamber includes a plurality of partitioned areas which sequester different parts of the apparatus into sectors. For example, one sector is an area where a waste trough is disposed and includes an outlet port extending through one of the upwardly extending side walls of the chamber. Similarly, a second sector is provided which circumscribes the shuttle means. The shuttle means includes a motor driven carriage assembly, a lead screw shaft and a cam shaft having a plurality of cams disposed thereon. A third sector is where a screw motor and a cam motor are housed and which communicate with the screw shaft and cam shaft respectively. The first and second sectors define part of a vacuum area of the chamber while the third sector is sealed from the vacuum area via a housing.

The vacuum control apparatus includes a vacuum pump which is operatively coupled to the vacuum area of the vacuum manifold via a vacuum line extending from the vacuum pump to the port of the waste trough. A liquid waste bottle is interposed between the vacuum pump and chamber and interrupts the vacuum line but not the vacuum therethrough. Thus, when the vacuum pump is turned on, the vacuum area of the chamber is depressurized and the vacuum power will pull the liquid from the sample plate during at least two processes detailed below.

A waste plate and a collection plate are disposed on a platform of the motor driven carriage assembly. The carriage assembly, carrying the collection plate and waste plate, is operatively coupled to the lead screw shaft via a lead screw block. The lead screw block is operatively coupled to the screw motor via the lead screw shaft. Thus, the lead screw motor may be actuated under the control of the electronic control system for linearly moving the carriage assembly between two lateral positions thereby placing either the collection plate or the waste plate under the sample plate. A cam pin disposed through the lead screw block aligns with one cam in each of these two lateral positions. Thus, the pin moves up or down by the coaction with one cam driven by the cam motor via the cam shaft. This results in bringing the collection plate or waste plate closer or further away from the sample plate.

At the outset of a sample treatment process the shuttle means will be controlled to move the waste plate underneath the sample plate via the coaction of the screw motor, lead screw shaft and lead screw block. A limit switch will provide positive feed back to the electronic control system in order to verify that the waste plate is properly indexed below the sample plate. At this time the electronic control system will actuate the cam motor to elevate the waste plate into communication with the sample plate. The vacuum area of the chamber is then depressurized via the vacuum pump apparatus and the waste liquid is pulled down from the sample plate and will flow through the waste plate and into the waste trough, out of the outlet port and then into a waste bottle. This waste removal process may be repeated depending on the sample being treated.

Once the waste from the sample plate has been properly disposed of, the electronic control system will actuate the screw motor to traverse the collection plate underneath the sample plate. A second micro-switch will feed back a signal to the control system when the collection plate is properly indexed below the sample plate. The electronic control system will then actuate the cam motor to lift the collection plate in communication with the sample plate and the vacuum pump apparatus will depressurize the vacuum area of the chamber for collecting the constituent or constituents of interest. Once the sample treatment has been completed the vacuum is released from the vacuum chamber and the top cover can be removed for retrieval of the collection plate for further sample analysis.

OBJECTS OF THE INVENTION

Accordingly, a primary object of the instant invention is to provide a new, novel and useful sample treatment system: apparatus and method.

A further object of the instant invention is to provide a sample treatment system as characterized above which includes a vacuum manifold apparatus with both waste and collection sites.

Another further object of the instant invention is to provide a sample treatment system as characterized above which includes a variable controlled vacuum extraction system including the vacuum manifold apparatus with both waste and collection sites and a digitally controlled variable speed vacuum pump apparatus.

Another further object of the instant invention is to provide a vacuum manifold apparatus as characterized above which includes an automated multi-position plate transportation mechanism.

Another further object of the instant invention is to provide a vacuum manifold apparatus as characterized above which includes an automated multi-position plate transportation mechanism including a stepper motor drive, positive position feedback and motor control means.

Another further object of the instant invention is to provide a vacuum manifold apparatus as characterized above which includes an automated multi-position plate lifting mechanism.

Another further object of the instant invention is to provide a vacuum manifold apparatus as characterized above which includes an automated multi-position plate lifting mechanism including a stepper motor drive, positive position feedback and motor control means.

Another further object of the instant invention is to provide a sample treatment system as characterized above which includes a variable control vacuum system comprising a microcontroller digital to analog control interface.

Another further object of the instant invention is to provide a sample treatment system as characterized above which includes an automated vacuum based waste extraction apparatus.

Another further object of the instant invention is to provide a sample treatment system as characterized above which includes a microcontroller interface system including a communication interface and in system programmability.

Another further object of the instant invention is to provide a sample treatment system as characterized above which is a stand alone functional module.

Viewed from the first vantage point, it is an object of the present invention to provide a sample treatment device; comprising in combination: a housing defining an enclosure; a sample plate; means to communicate a sample plate with an interior of the housing; extraction means operating on the sample plate addressing the sample plate to the housing in fluid communication, and receptor means within the housing including shuttle means to selectively address an area below the sample plate for the throughpassage of fluid from the sample plate.

Viewed from the second vantage point, it is an object of the present invention to provide a method for treating a sample, the steps including: providing a housing defining an enclosure; nesting a sample plate at least partially within the enclosure wherein the sample plate is in open fluid communication with an interior of the enclosure and exteriorly; shuttling a receptor means within the enclosure to selectively address an area below the sample plate; evacuating air from the enclosure to a degree below atmospheric pressure for through passage of a fluid from the sample plate to the receptor means.

Viewed from the third vantage point, it is an object of the present invention to provide a sample treatment device;

comprising in combination: a housing defining an enclosure including means for receiving a sample plate in open fluid communication with an interior of said enclosure and exteriorly; means for supporting both a waste plate and a collection plate in horizontal plan; means for laterally traversing both the plates to selectively address one of the plates to an area below the sample plate; means for vertically traversing both the plates to selectively address one of the plates with the sample plate; means for evacuating air from the enclosure to a degree below atmospheric pressure for through passage of a fluid from the sample plate to the plate laterally and vertically addressing the sample plate.

These and other objects will be made manifest when considering the following detailed specification when taken in conjunction with the appended drawing figures.

BRIEF DESCRIPTION OF THE DRAWINGS

FIG. 5 is a partial exploded parts view of that which is shown in FIG. 4 and having a collection plate and waste plate removed therefrom.

FIG. 16 is a schematic depiction of sample collection according to the instant invention.

DESCRIPTION OF PREFERRED EMBODIMENTS

Figure 1:
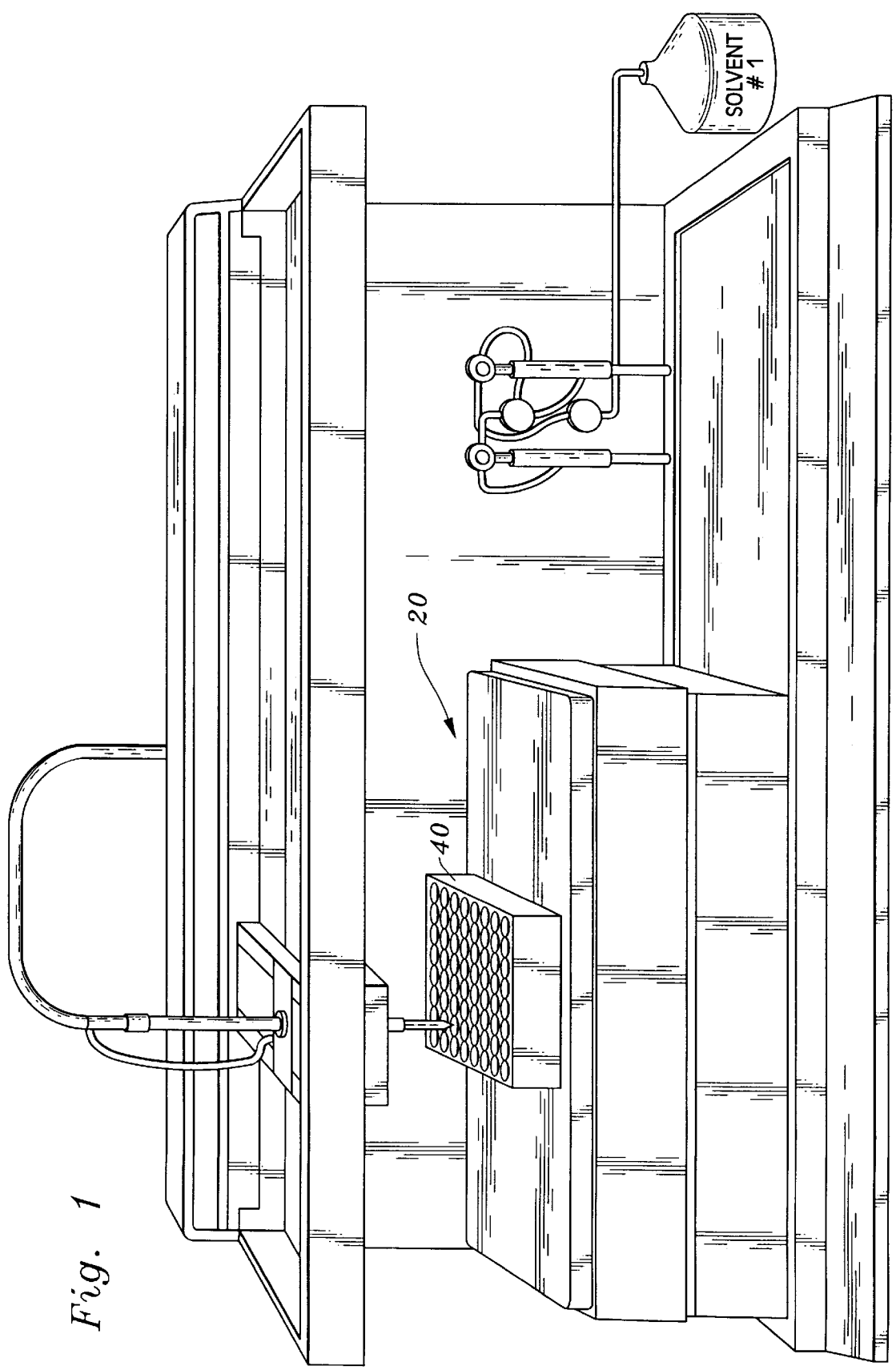
FIG. 1 is a front side elevational view of the vacuum manifold apparatus shown disposed on a robotic sample processor.

Considering the drawings, wherein like reference numerals denote like parts throughout the various drawing figures, reference numeral 10 is directed to the sample treatment system according to the present invention.

Referring to FIG. 1, a vacuum manifold apparatus 20 of a sample treatment system 10 is shown disposed on a top surface of a liquid handling system tailored for automatic extraction of genomic and plasmid DNA or solid phase extraction of compounds, but not limited to such applications. The liquid handling system or robotic sample processor permits a wide range of liquid handling operations. To transfer and add liquids to, for example, a 96 well filter plate 40, a probe is mounted on an XYZ translator mechanism above a vacuum manifold apparatus 20. The probe or a plurality of probes may be translated in the X and Y dimensions above the structure and also may be raised and lowered in the Z dimension. Metered amounts of liquids can then be supplied to the plurality of columns arranged in an eight by twelve matrix forming the 96 well filter plate 40 including a sorbing material or frit as is know in the art.

Figure 2:
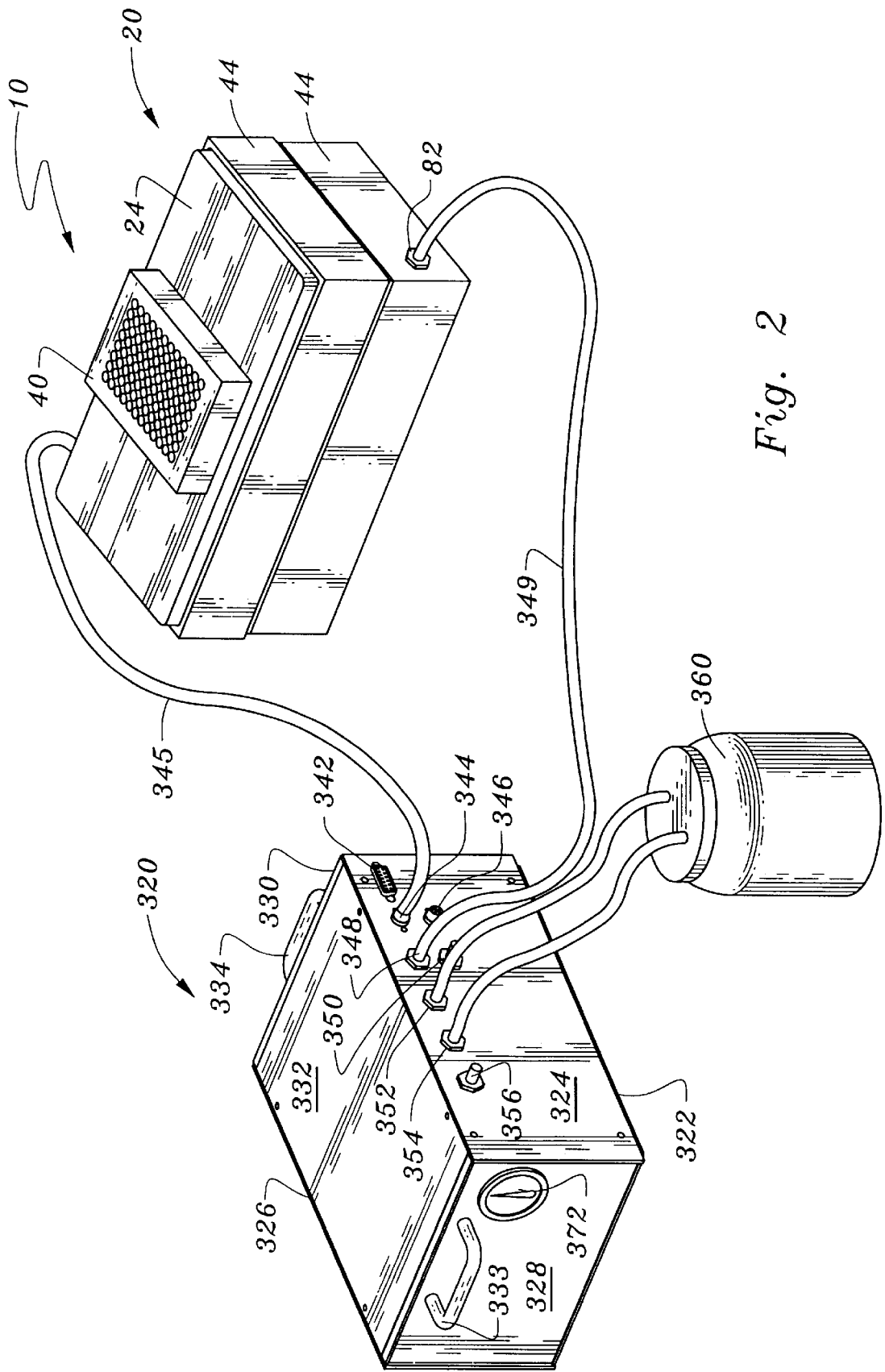
FIG. 2 is an elevational view of a vacuum pump apparatus and a vacuum manifold apparatus according to the instant invention.

Referring to FIG. 2, the sample treatment system 10 includes a vacuum manifold apparatus 20 and a vacuum control apparatus 320. The vacuum manifold apparatus 20 includes a housing defined by an open top chamber 44 and a housing cover 24 disposed thereon. The housing cover 24 includes a centralized opened ended well 34 (please see FIG. 6) for receiving the filter plate 40, for example, a solid phase extraction filter 40 which nests therein. The vacuum manifold apparatus 320 is preferably substantially rectangular in shape and includes a planar bottom surface 322 having an outer periphery with upwardly extending side walls defined by a front panel 324, a rear panel 326, a left side panel 328 and a right side panel 330. A top panel 332 completes the housing thereby defining a rectangular shaped enclosure having a hollow interior. Handles 333 and 334 are disposed on the side panels 328 and 330 respectively for user convenience in transporting the vacuum control apparatus 320. The vacuum control apparatus 320 is operatively coupled to the vacuum manifold apparatus 20 via a command feedback powerline 345 and vacuum line 349 which will be described infra. Furthermore, there is a communication port 342 which communicates with a processor/controller 380 (FIG. 14), two command feedback power ports 344, 346 four vacuum ports 348, 350, 352, 354, and an exhaust port 356 all disposed on the front panel 324 of the vacuum control apparatus 320 and which will described hereinbelow. Note that ports 352, 354 operatively communicate with a containment chamber 360 which will also be described infra.

Figure 3:
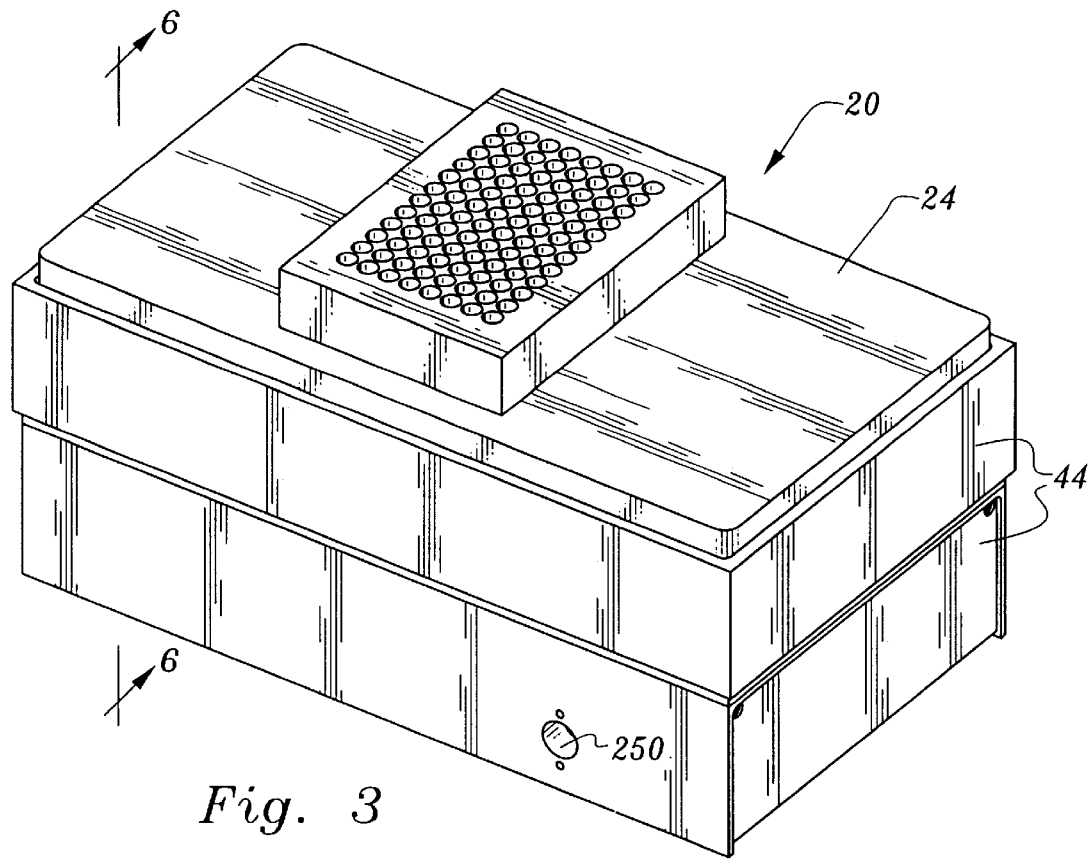
FIG. 3 is a front side elevational view of the vacuum manifold apparatus according to the instant invention.

Referring to FIG. 3, a front elevational view of the vacuum manifold apparatus 20 is shown to reveal a command feedback powerline port 250 which allows the command feedback powerline 345 to operatively couple between command feedback power port 344 and port 250 and onto motors 260, 270 (please see FIG. 5).

Figure 4:
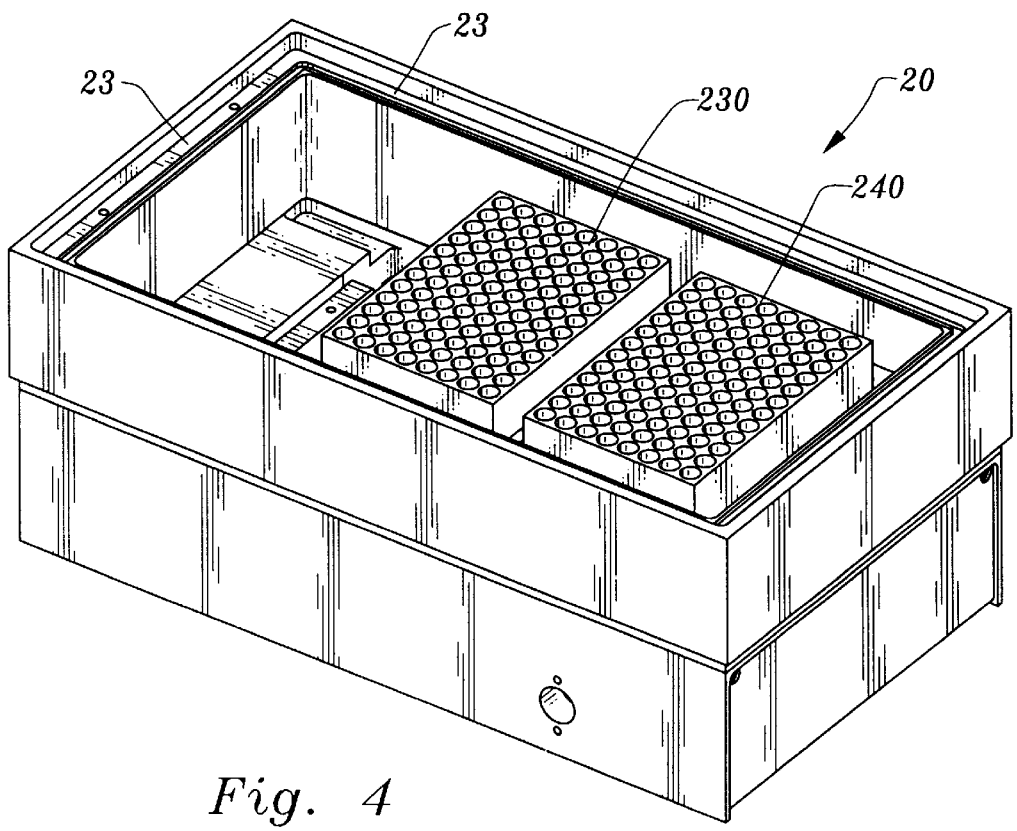
FIG. 4 is a front side elevational view of the vacuum manifold apparatus having a top cover removed therefrom.

FIG. 4 shows the vacuum manifold apparatus 20 with the housing cover 24 removed therefrom thereby revealing a circumscribing flange 23 in which the housing cover 24 sits and then seals under a vacuum. The interior of the housing includes a waste plate 230 and a collection plate 240.

Figure 13:
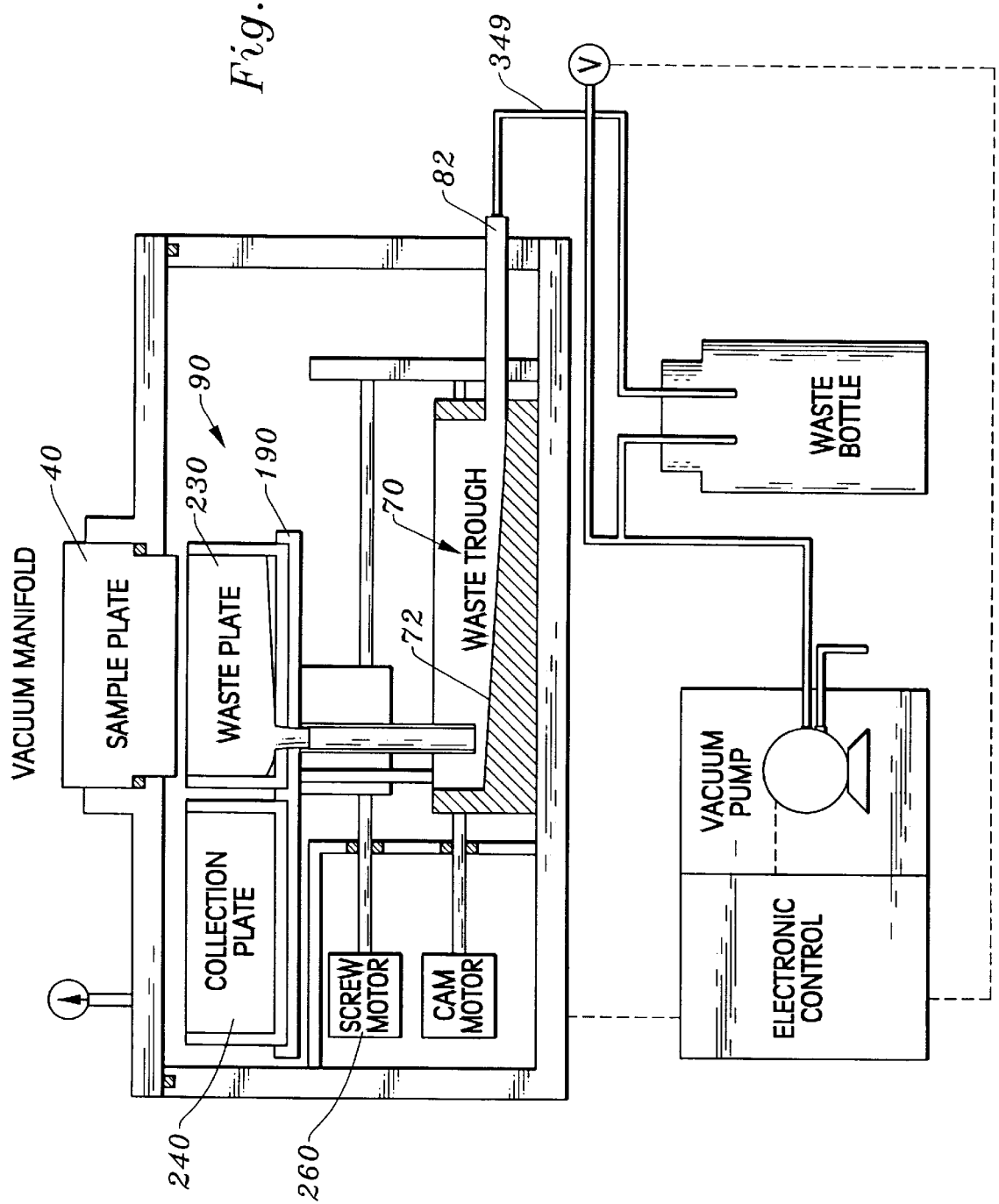
FIG. 13 is a schematic view of that which is shown in FIG. 2.

Referring to FIG. 5, an exploded parts view is shown detailing the chamber 44 and the parts disposed therein. Chamber 44 includes an upper housing 46 and a lower housing 56, the lower housing 56 which includes a substantially planar bottom surface 58 (FIG. 6) having an outer periphery with upwardly extending walls 62, 64, 66 and 176. The interior of the lower housing includes a plurality of partitioned areas which sequester different parts of the apparatus 20 into sectors. For example, one sector is an area which includes a waste trough 70 preferably integrally formed with the lower housing 56. The waste trough 70 longitudinally extends along the back wall 64 of the lower housing and includes a longitudinally extending front wall surface 78, a longitudinally extending back wall surface 80, a latitudinally extending left side wall 74 and a latitudinally extending right side wall 76. In addition, the waste trough 70 includes a tapered bottom surface 72 (FIG. 13) which tapers to the side wall surface 74 wherein a drain plug 82 (FIG. 2) is disposed which operatively communicates with the vacuum line 349 and thus the vacuum control apparatus 320. A second sector is provided which defines a shuttle means well 88 which circumscribes a shuttle means 90 which will be described infra. A third sector is where the screw motor 260 and the cam motor 270 are housed and is defined by an enclosure formed by a portion of the front and back wall 62, 64, and a L shaped plate defining a substantially planar bottom wall 174 and the side wall 176 which also defines the right side wall of the lower housing 56. In addition, to complete the enclosure a right carriage plate 96 doubles as a side wall which is spaced from the right side wall 176 thereby defining an enclosure which seals the motors 260, 270 from a vacuum area.

Figure 6:
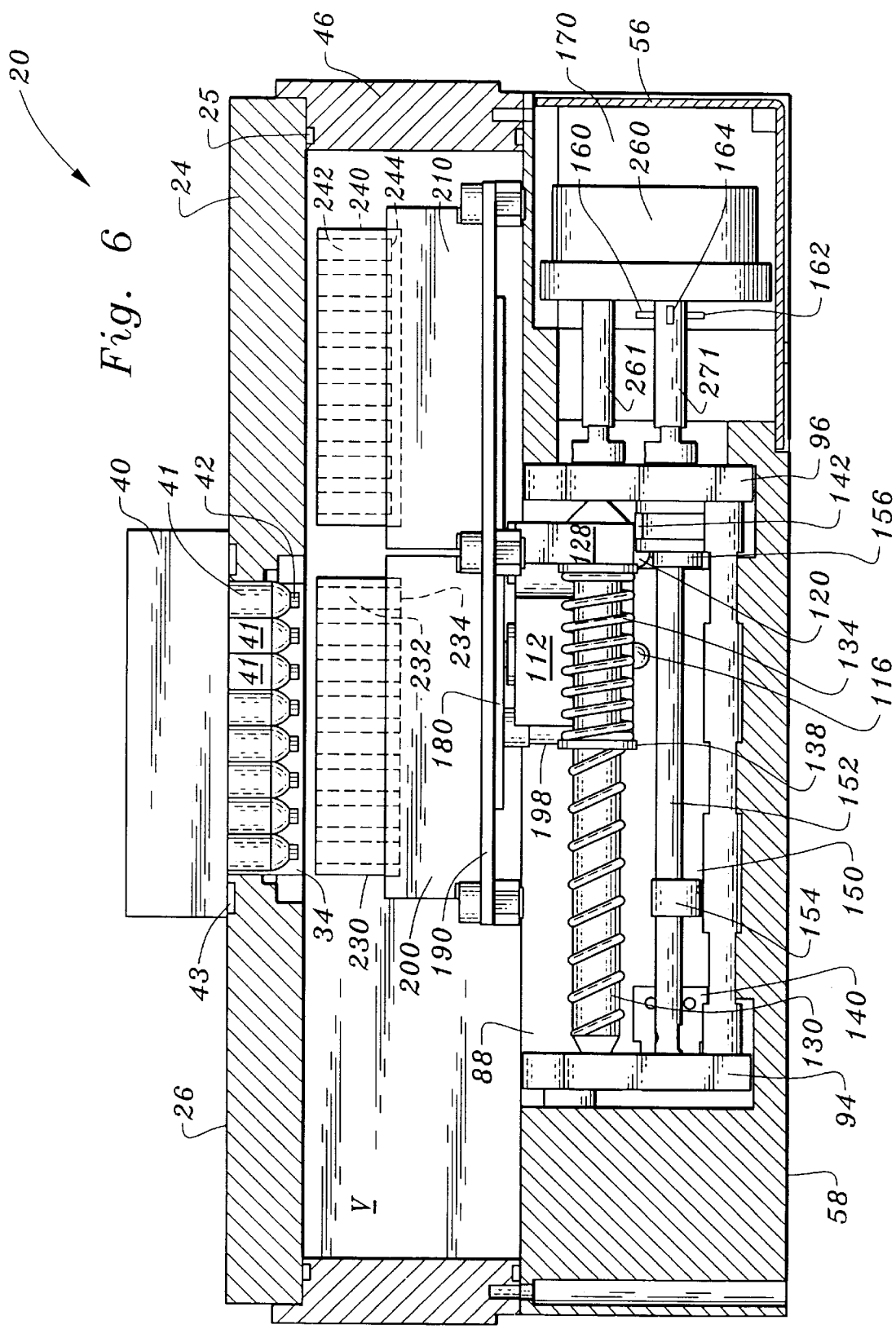
FIG. 6 is a cut-away view along the double-ended arrows shown in FIG. 3.

FIGS. 5 and 6 also detail a carriage spacer plate 180 which operatively couples to a carriage 112. The carriage spacer plate 180 is substantially rectangular and uniform in thickness and includes a pair of apertures 182, 184. The apertures 182, 184, receive a guide pin 116 and an elevating pin 120 which are received into the carriage 112 via respective bores 114, 118. The top extremities of the guide pin 116 and elevating pin 120 are preferably flanged to preclude the pins from dropping completely through the apertures 182, 184. A plate platform 190 rides on top of the spacer plate 180 and is also substantially rectangular in shape. The plate 190 can be provided with apertures 192, 194 for allowing fastening means to fasten to guide pin 116 and elevating pin 120. Platform 190 further includes a spout bore 196 in which a spout 198 is received therein. The platform 190 serves as a support for a waste tray 200 and a collection tray 210 which receive and retain waste plate 230 and collection plate 240 respectively. The waste tray 200 is provided with a tapered bottom surface 204 which tapers into a waste tray bore 202 which communicates with the spout 198. The upper housing 46 frames the platform 190, waste tray 200, collection tray 210, waste plate 230, and collection plate 240. The upper housing 46 is a substantially rectangularly shaped open ended structure including spaced apart longitudinally extending side walls 48, 50 and parallel spaced apart latitudinally extending side walls 52, 54.

Referring to FIG. 6, a cut-away view along the double-ended arrow 6—6 of FIG. 3 is shown. The filter plate 40 is shown nesting within the centralized well 34 of the housing cover 24. The filter plate preferably includes a circumscribing flange 43 which abuts a top surface 26 of the housing cover 24 to preclude further movement of the filter plate within the well 34. The filter plate preferably includes a plurality of columns 41, for example, an eight by twelve matrix of columns and is typically referred to as a 96 well plate. Each column includes an orificed top as shown in FIG. 3 and an orificed bottom 42 as shown in FIG. 6 and a sorbing material or frit as is known in the art. The shuttle means 90 is shown in a position wherein the waste plate 230 is directly below the filter plate 40. The waste plate 230 includes a complemental eight by twelve matrix of open ended bores 232 thereby allowing fluid to flow from the columns 41 of the filter plate 40 and pass through the bores 232 and into the waste tray 200. The orificed bottoms 42 of the columns 41 partially extend within the respective open ended bores 232 to preclude cross-talk between the orificed columns 41 of the filter plate 40. The collection plate 240 is shown juxtaposed to the waste plate 230 and includes the same eight by twelve matrix pattern as is found in both the waste plate and filter plate. The collection plate includes 96 blind bores 242 each having an opened end 243 as shown in FIG. 4 and a closed end 244.

Figure 7:
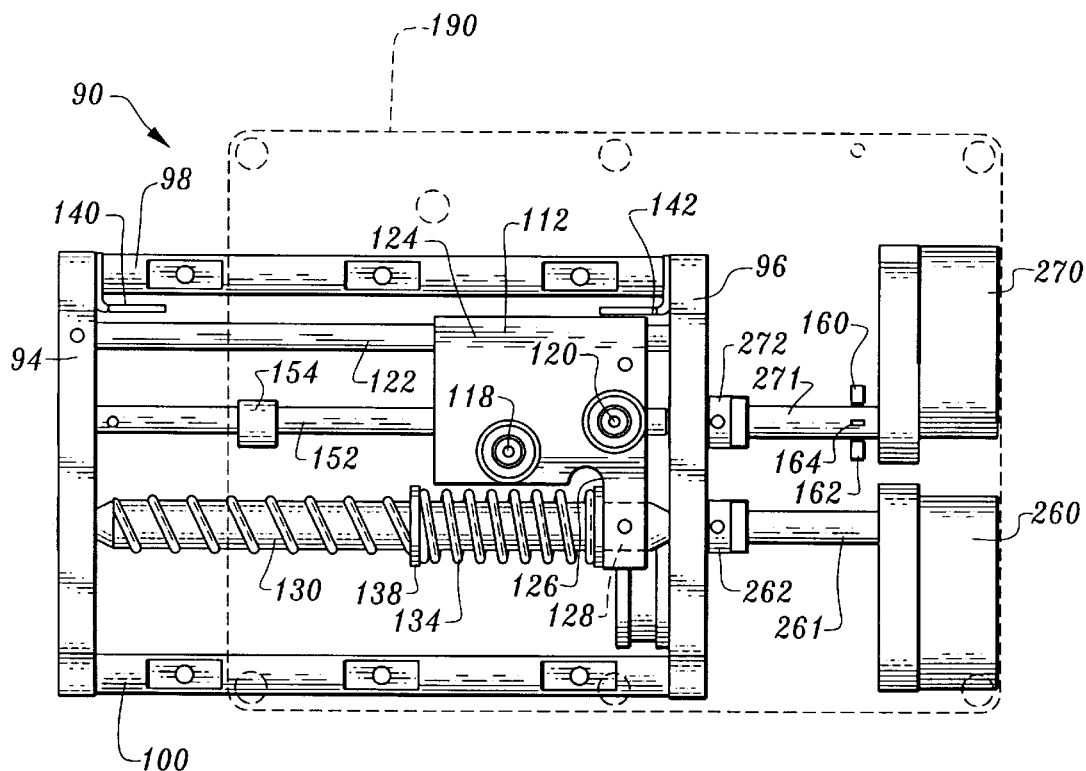
FIG. 7 is a top plane view of the shuttle mechanism including a cam drive motor and a screw drive motor according to the instant invention.

The waste plate 230 nests within the tray 200 and the collection plate 240 nests within the tray 210. The waste tray 200 and the collection tray 210 both are supported by the plate platform 190 which is operatively coupled to the carriage 112. Specifically, the platform 190 is movably coupled to the spacer plate 180 via the coaction of the elevating pin 120 with either cam 154 or 156. In addition, guide pin 116 helps provide guidance of the up and down motion promulgated by the coaction of the cams with the elevating pin 120 which will be described in detail hereinbelow. A cam shaft 152 rigidly maintains cams 154 and 156 in a spaced apart relationship and at one end, the cam shaft 152 is operatively coupled to the carriage plate 94 and at the other end the cam shaft 152 communicates with a drive shaft 271 via a coupling 272 (FIG. 7) through the right carriage plate 96. In addition, a lead screw 130 is shown operatively coupled to the left carriage plate 94 via, preferably, a bushing. The opposite end of the lead screw 130 is operatively coupled through carriage plate 96 to a drive shaft 261 of the motor 260 via a coupling means 262 (FIG. 7). A bias means in the form of a spring 134 and a bobbin shaped structure 138 takes up the play between the lead screw 130 and the carriage 112.

The shuttle means 90 provides positive feedback both for lateral movement and vertical movement of the platform 190. Preferably, a pair of micro-switches 140 and 142 are disposed at left and right extremities in which the carriage 112 traverses. In addition, a pair of micro-switches 160, 162 are place adjacent the cam motor drive shaft 271 wherein a tab 164 actuates one or the other when the platform 190 is reciprocated in an up and down vertical motion. Preferably, the motors 260, 270 are sealed in the motor housing 170 and are sealed from the vacuum chamber V which preferably includes the interior of the upper housing and the interior of the lower housing which includes waste trough 70.

Referring to FIGS. 7 through 10, the shuttle means 90 will now be explained in detail. The shuttle means 90 can generally be regarded as having a base frame formed from a pair of spaced parallel bar members 98, 100 interconnected at one extremity by the left carriage plate 94 and at the other extremity by the right carriage plate 96. Preferably, the bar members 98, 100 are rigidly attached to the left and right carriage plates at their extremities thereof. The lead screw motor 260 and cam drive motor 270 lie outside of the opened rectangular grid area defined by the pair of spaced parallel bar member 98, 100 and the spaced parallel carriage plate members 94, 96. The lead screw motor 260 includes a motor shaft 261 which is coupled to the lead screw 130 via a coupling 262. Preferably, a sealed bushing is disposed in carriage plate 94 and carriage plate 96 for supporting the ends of the lead screw 130. The lead screw 130 operatively couples to the carriage 112 by extending through a bore 128 in an arm 126 of the carriage 112. A bias spring 134 and bobbin 138 bias the lead screw to the carriage 112 to preclude play therebetween.

The cam drive motor 270 includes a drive shaft 271 which is coupled to the cam shaft 152 via a coupling 272. Preferably, the cam shaft is rotatably supported at each of its extremities via a sealed bushing being disposed in each of the carriage plates 94, 96. A guide rail 122 is interposed between the cam shaft 152 and rod 98 for providing guidance to the carriage 112 when the carriage traverses from one lateral position to another along doubled ended arrow "B" shown in FIG. 9. The guide rail 122 extends through the carriage 112 via a carriage guide bore 124 (FIG. 10). Note that micro-switches 140, 142 coact with the carriage 112 to provide positive feedback of the lateral position of the carriage 112. The vertical up and down positioning of the platform 190 is provided by coaction of a lobe area of the cam coming in contact with the elevating pin 120 when the cam shaft 152 is rotated by the cam drive motor 270. Note that the cams 154, 156 only coact with the lift pin 120 when the carriage 112 is in one lateral extreme position or the other.

Figure 8:
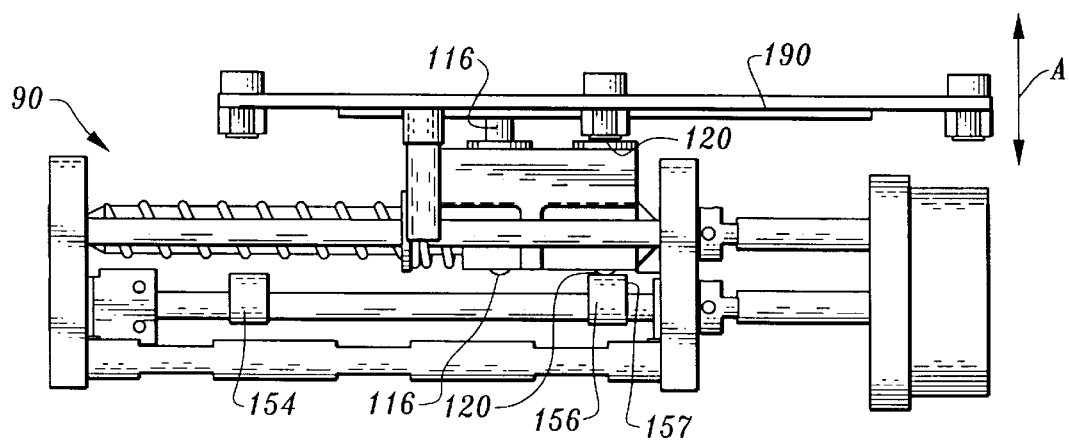
FIG. 8 is a side plane view of the shuttle mechanism according to the instant invention.

Referring to FIG. 8, the platform 190 is shown in an elevated position by the coaction of a lobe 157 of the cam 156 and the elevating pin 120. This position would by correlative to the waste plate 230 being in liquid communication with the filter 40 during the waste extraction process.

Figure 9:
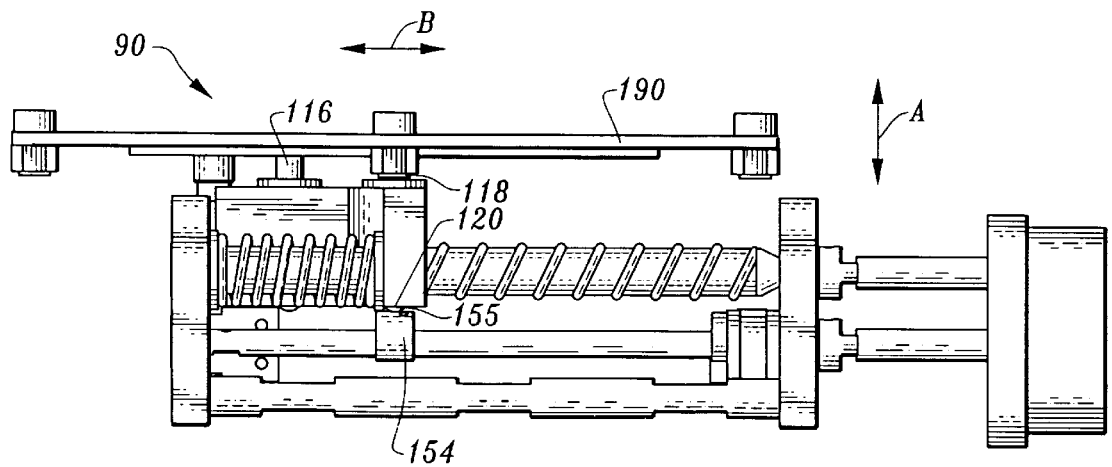
FIG. 9 is an opposite side plane view of that which is shown in FIG. 8.
Figure 10:
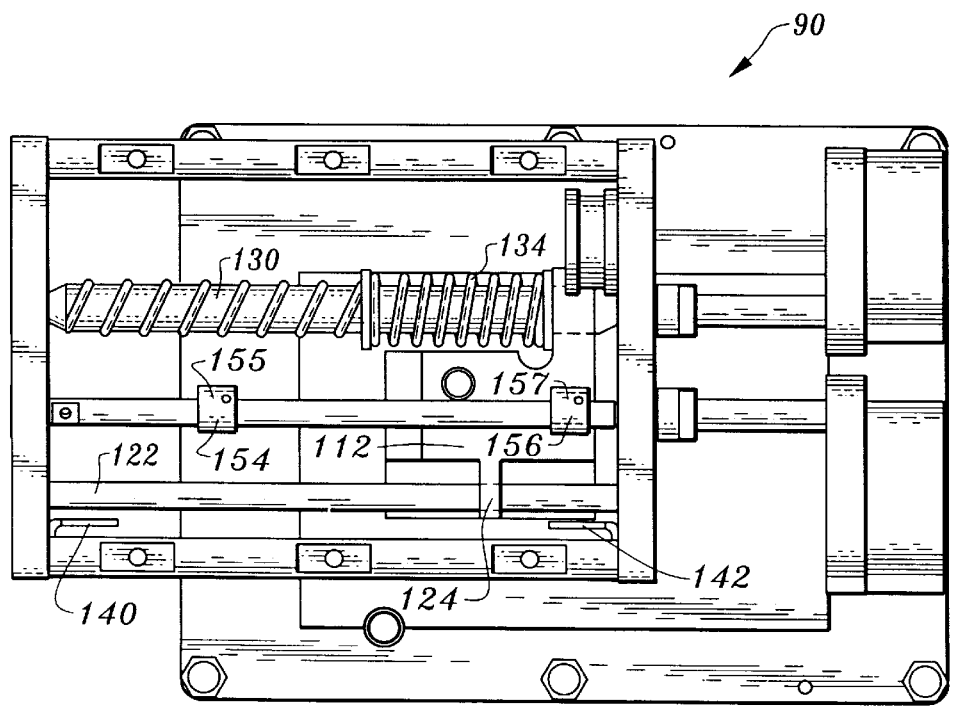
FIG. 10 is a bottom plane view of the shuttle mechanism.

Referring to FIG. 9, the platform 190 is shown in a second lateral position and elevated. In an elevated position, as shown, a cam lobe 155 of the cam 154 will coact with the elevating pin 120 to allow the collection plate 240 to be in liquid communication with the filter plate 40. The orificed bottoms 42 of the columns 41 partially extend into respective closed ended bores 242 in this elevated position to preclude cross-talk.

Referring to FIG. 10, a bottom plane view of the shuttle means 90 is shown to reveal detail of the cams 154, 156, the carriage 112 and the lead screw 130 with the associated biasing means 134. Specifically, the lobe 155 of the cam 154 and the lobe 157 of the cam 156 are clearly shown. In addition, clear detail of how the guide rail 122 passes through the carriage 112 via the bore 124 can also be discerned.

Figure 11:
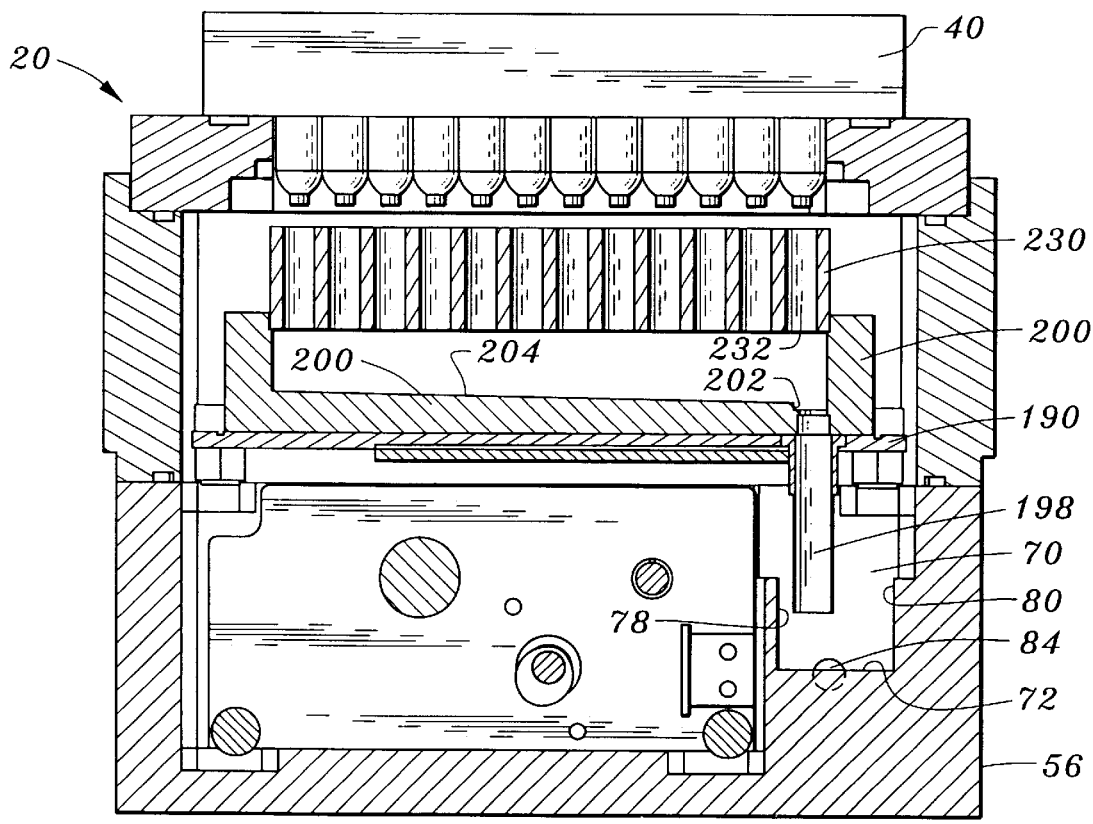
FIG. 11 is a cross sectional view of the vacuum manifold apparatus detailing a well disposed in a top cover, a sample waste rack, a waste tray and a waste trough.

Referring to FIG. 11, a cross-sectional view of the vacuum manifold apparatus 20 is shown. This reveals detail of the waste tray 200, the spout 198 and the waste trough 70. Specifically, the waste trough 70 is integrally formed within the lower housing 56 and provides further clarity of the bottom surface 72, the front side surface 78 and the rear side surface 80. A bore 84 shown in phantom is the bore in which the drain plug 82 operatively couples through (please see FIG. 2). The spout 198 extends from within the waste trough 70 and terminates at a location within the waste tray bore 202.

Figure 12:
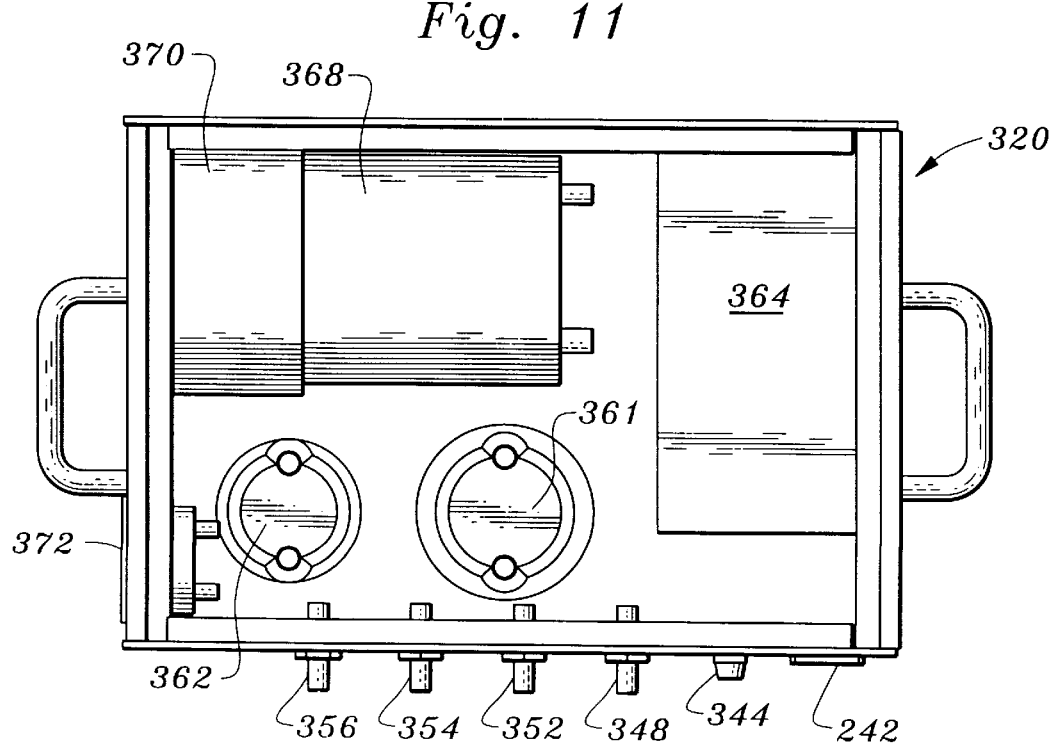
FIG. 12 is a top plane view of a vacuum pump apparatus according to the instant invention.

Referring to FIGS. 2 and 12, the automated sample treatment system 10 includes the vacuum control apparatus 320. The vacuum control apparatus 320 includes a vacuum pump 368 which is operatively coupled to the chamber 44 via a three-way valve 361. The three-way valve 361 is coupled to vacuum line ports 348, 350 which are in turn coupled to the drain plug 82 via vacuum line 349 for providing vacuum within the chamber 44. Note that each vacuum port 348, 350 can be operatively coupled to two separate vacuum manifolds 20 for providing vacuum thereto. The liquid waste bottle or containment chamber 360 is interposed between the vacuum pump 368 and vacuum manifold apparatus 20 to interrupt the vacuum line but not the vacuum provided therethrough. Thus, when the vacuum pump is turned on, the vacuum chamber area is depressurized and the vacuum power will pull the liquid from the sample plate 40 during two processes which will be delineated hereinbelow. In addition, the vacuum power will pull the liquid through the waste trough and into the waste bottle. The vacuum control apparatus further includes a pump controller 370 for controlling the vacuum pump and a vacuum controller 364 for, inter alia, providing commands to the vacuum manifold apparatus 20, receiving feedback from the vacuum manifold apparatus 20 and providing power thereto.

The vacuum control apparatus 320 includes a manual vacuum gage operatively coupled to the vacuum pump 368 to monitor the vacuum being provided to the vacuum manifold apparatus 20. In addition, an exhaust valve or shut-off valve 362 is used to provide atmospheric pressure back into the vacuum manifold apparatus 20.

Figure 14:
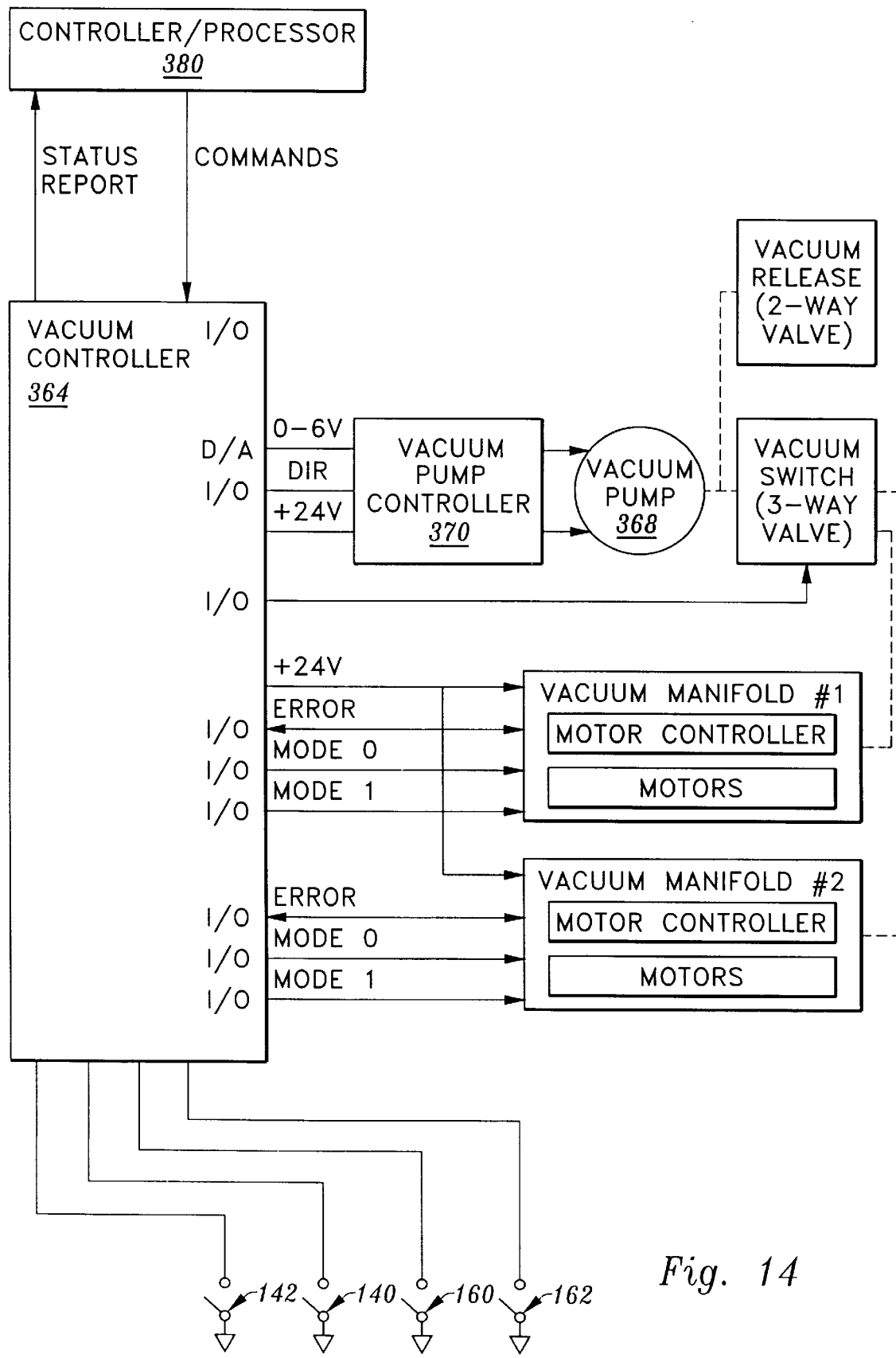
FIG. 14 is a schematic view of an electronic control system according to the instant invention.
Figure 15:
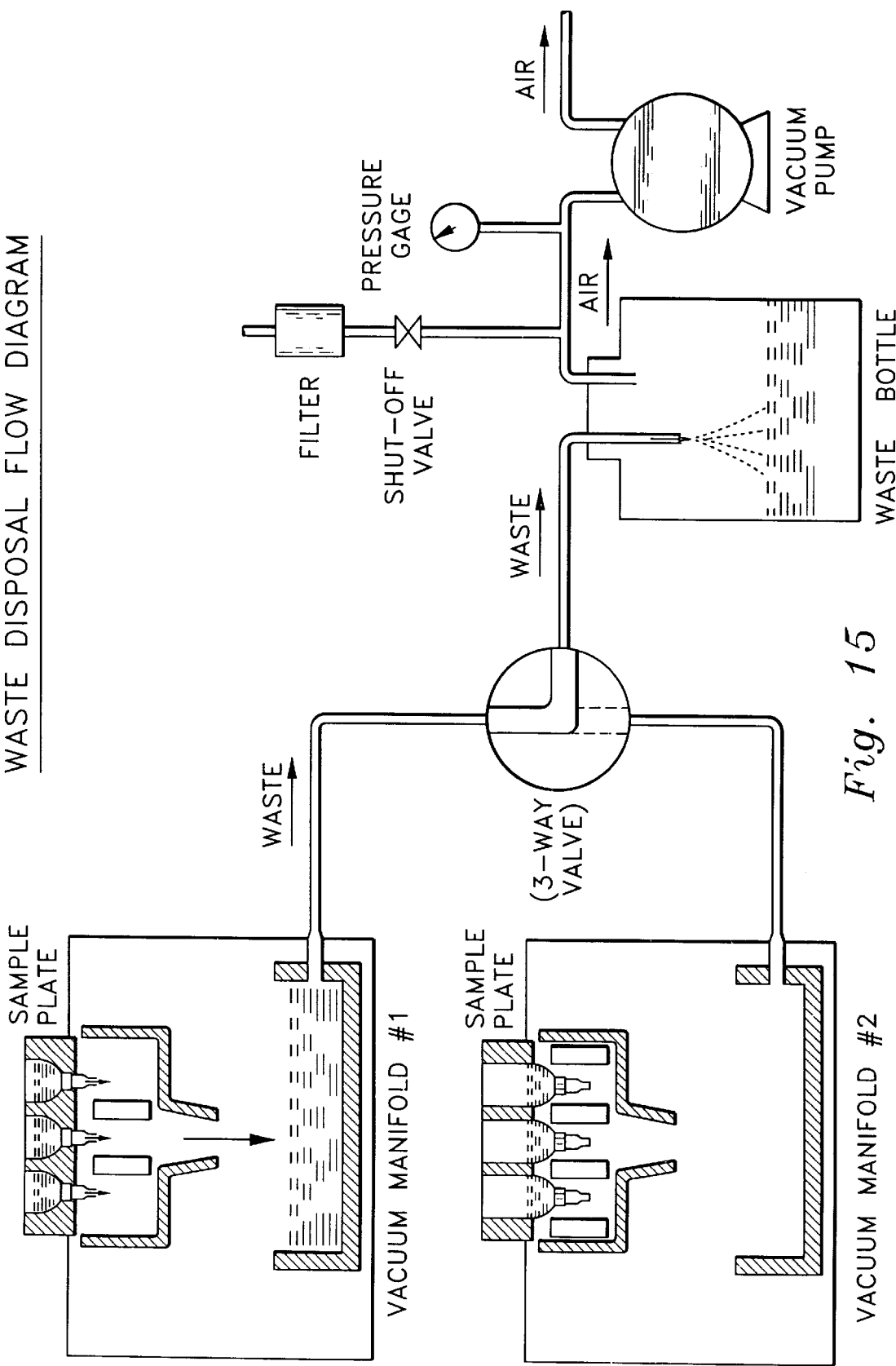
FIG. 15 is a schematic depiction of waste disposal according to the instant invention.

In use and operation, and referring to FIGS. 13 through 16, at the outset of a sample treatment process, liquid is transferred to the sample plate 40. The shuttle means 90 will then be actuated to move the waste plate 230 in liquid communication with the sample plate 40. Specifically, a motor controller will receive signals from a vacuum controller 364 to actuate the screw motor 260 to laterally move the platform 190 in a position wherein the waste plate is directly below the sample plate. Precise positioning of the waste plate underneath the sample plate will be provided by the carriage 112 coacting with the micro-switch 142 to provide positive feedback to the vacuum controller 364 in order to verify that the waste plate 230 is properly indexed below the sample plate 40. At this time the vacuum controller 364 will communicate with the motor controller to drive the cam motor 270 in order to elevate the waste plate 230 in liquid communication with the sample plate 40. Positive vertical position feedback will be provided by micro-switch 160 sending a signal to the vacuum controller 364 to assure that correct lift has been obtained. When the vacuum controller has received both a positive position feedback of the horizontal travel and vertical lift positions it will send the signal to the vacuum pump controller which will in turn actuate the vacuum pump to apply vacuum to the vacuum manifold apparatus 20. Referring to FIG. 15, this will cause the liquid in the sample plate 40 to be pulled down into the waste plate 230 and then out through the waste trough 70 via a three way valve 361 and into the waste bottle 360. Once the waste liquid is pulled down from the sample plate 40 and evacuated out to the waste bottle 360 the vacuum pump will be deactivated under the control of the vacuum controller. Next, the vacuum controller will send a signal to the motor controller to actuate the cam motor to disassociate the waste plate from the sample plate and then will send a second signal upon receiving positive feedback from the down micro-switch 162 which actuates the screw motor to traverse the collection plate underneath the sample plate. Once the vacuum controller has received positive feedback from the second horizontal position switch 140 it will initiate a signal to the motor controller to actuate the cam motor. The cam motor will then provide the motive means to place the collection plate 240 in liquid communication with the sample plate 40 and this position will be verified by the up micro-switch 160 providing positive feedback to the vacuum controller.

Referring to FIG. 16, once the collection plate is properly indexed below the sample plate 40 the vacuum controller 364 will communicate with the vacuum pump controller to actuate the vacuum pump 368 to depressurize the vacuum chamber and draw the constituent or constituents of interest from the liquid sample into the collection plate. Once the sample treatment process has been completed and the constituent or constituents have been collected into the collection plate the vacuum controller will send a signal to the motor controller to actuate the cam motor to place the platform 190 and thus the collection plate in the down position which will be verified by positive feedback being provided from the down micro-switch 162 to the vacuum controller 364. In addition, the vacuum controller will send a signal to the vacuum pump controller 370 to de-activate the vacuum pump 368 and then an exhaust valve will be actuated under the control of the vacuum controller to provide atmospheric pressure back into the vacuum manifold apparatus 20. Thus, the housing cover 24 which has been sealed onto the chamber 44 via the vacuum therein may be removed to allow a user access to the collection plate. The collection plate is then removed for further analysis of the constituent or constituents which have been collected therein. Note that both the waste disposal steps and the sample collection steps can be done under a variable vacuum condition via a digital to analog interface between the vacuum controller and the vacuum pump controller as shown in FIG. 14.

A main controller/processor 380, which is preferably associated with the liquid handling system, can orchestrate the entire automated sample treatment process by being operatively coupled to the vacuum controller 364 and providing orchestrating commands thereto and receiving status reports therefrom. Furthermore, the vacuum control apparatus 320 may be operatively coupled to two separate vacuum manifolds and provide vacuum thereto under the control of a vacuum switch or three way valve as is shown in FIGS. 14 through 16.

The automated sample treatment system 10 can provide sample treatment in the form of, inter alia, a pretreatment of fluid to lyse cellular components or dilute samples, provide a conditioning treatment which pre-treats the filter 40 to hydrate or functionalize the sorbent. In addition, the sample treatment system 10 can apply a vacuum over the waste plate to start an extraction process. Furthermore, a wash solution/solvent may be added to the filter plate and then the vacuum may be applied over the waste container to remove undesired elements from the filter plate. Furthermore, an elution buffer/solvent may be added to the filter plate and then vacuum may be applied over the collection plate to extract the desired compounds.

The sample treatment system 10 provides an air tight container to allow vacuum to be developed below the filter sample plate 40, and then drives the shuttle means 90 to allow lateral motion of the platform 190 thus placing the waste or collection plate below the filter sample plate 40 which are carried thereby, and then elevates the waste or collection plate directly below the filter sample plate 40 to minimize cross-talk of the sample being treated and then actuates a waste extraction means to automatically remove waste into the waste plate and from inside the vacuum manifold apparatus 20 or to collect constituents into the collection plate.

Moreover, having thus described the invention, it should be apparent that numerous structural modifications and adaptations may be resorted to without departing from the scope and fair meaning of the instant invention as set forth hereinabove and as described hereinbelow by the claims.

We claim:

1. A sample treatment device, comprising in combination:
a housing defining an enclosure;
a sample plate having an open top and open bottom with plural sample specimens therein;
means on a top of said housing to support said sample plate and expose said open bottom of said sample plate to an interior of said housing;
extraction means drawing on said open bottom of sample plate and into said housing in fluid communication, and
receptor means within said housing including vertical shuttle means to juxtapose said receptor means proximately below said sample plate to receive fluid from said sample plate and prevent cross talk between said plural sample specimens.

2. The device of claim 1 wherein said extraction means includes a variable control vacuum system operatively coupled to said housing for evacuating air from said enclosure at variable rates for providing variable flow rate recovery and throughput of compounds.

3. The device of claim 2 wherein said housing includes an opened chamber and a housing cover disposed thereon, said housing cover having an opened ended well for receiving said sample plate wherein said sample plate is an open fluid communication with said interior of said housing and exteriorly.

4. The device of claim 3 wherein said sample plate includes an integrally formed matrix of columns each including a sorbing material therein.

5. The device of claim 1 wherein said receptor means includes a collection plate and a waste plate juxtaposed to each other in a horizontal plane, said collection plate including a plurality of blind bores disposed in a spaced apart relationship and said waste plate including a plurality of open ended bores disposed in a spaced apart relationship.

6. The device of claim 5 further including a waste tray and a collection tray for receiving said waste plate and said collection plate respectively.

7. The device of claim 6 wherein said waste tray includes a tapered bottom surface tapering into a waste tray bore in communication with a downwardly extending spout.

8. The device of claim 7 further including a trough within said housing, said trough in liquid communication with said spout for receiving waste which passes through said sample plate and into said waste plate under the operation of said extraction means for extracting said waste exteriorly of said housing.

9. The device of claim 8 wherein said shuttle means includes a platform supporting both said waste tray and said collection tray on an upper surface thereof.

10. The device of claim 9 wherein said shuttle means further includes a carriage operatively coupled to said platform and to both a vertical motive means and horizontal motive means for laterally and horizontally moving both said waste plate and said collection plate to selectively address the area below said sample plate for the through passage of fluid from said sample plate.

11. The device of claim 10 wherein said horizontal motive means includes a lead screw operatively coupled to said carriage and to said horizontal motive means.

12. The device of claim 11 wherein said carriage is spring biased to said lead screw to preclude play therebetween.

13. The device of claim 12 further including a cam shaft operatively coupled to said vertical motive means and rigidly supporting a pair of cams in a spaced apart relationship.

14. The device of claim 13 further including means to operatively couple said platform to either cam for providing lift from one horizontal plane to another horizontal plane when said vertical motive means is actuated.

15. The device of claim 1 further including positive position feedback means operatively coupled to said shuttle means for providing precise horizontal positioning of said receptor means below said sample plate.

16. The device of claim 1 further including positive position feedback means operatively coupled to said shuttle means for providing precise vertical positioning of said receptor means below said sample plate.

17. A method for treating a sample, comprising the steps of:
providing a housing defining an enclosure having an opening in a top thereof;
nesting a sample plate having multiple specimens therein at least partially within the top of the enclosure wherein the sample plate is in open fluid communication with an interior of the enclosure;

shuttling a receptor means horizontally and vertically within the enclosure thereby juxtaposing the receptor means proximate a bottom of the sample plate;

evacuating air from the enclosure to a degree below atmospheric pressure for through passage of a fluid from the sample plate to the receptor means without cross talk of the specimens.

18. The method of claim 17 wherein the shuttling step further includes the step of shuttling a waste receptor within the enclosure to selectively address the area below the sample plate.

19. The method of claim 18 wherein the evacuating step further includes the step of evacuating air from the enclosure to a degree below atmospheric pressure for through passage of fluid waste from the sample plate to the waste receptor.

20. The method of claim 19 further including the step of evacuating the fluid waste from the waste receptor and enclosure.

21. The method of claim 20 wherein the shuttling step further includes shuttling a collector receptor within the enclosure to selectively address the area below the sample plate.

22. The method of claim 21 wherein the evacuating step further includes evacuating air from the enclosure to a degree below atmospheric pressure for through passage of a constituent from the sample plate to the collector receptor.

23. The method of claim 22 further including the step of replenishing air pressure within the enclosure and removing the collector receptor for further constituent analysis.

24. A sample treatment device, comprising in combination:

a housing defining an enclosure including means for receiving a sample plate in open fluid communication both with an interior of said enclosure and exteriorly;

means for supporting both a waste plate and a collection plate in a horizontal plane;

means for laterally translating both said waste and collection plates to selectively orient either said waste or collection plate to an area below the sample plate;

means for vertically moving both said plates to selectively place either said waste or collection plate next to the sample plate;

means for evacuating air from the enclosure to a degree below atmospheric pressure to pull a fluid from the sample plate to either said waste or collection plate when adjacent said sample plate.

25. A device to move fluid from a sample plate having plural samples oriented in open bottomed vertical tubes to a collection plate having a complemental number of open topped vertical tubes as the sample plate, comprising, in combination:

an enclosure to support the sample plate substantially horizontally;

a vacuum means in said enclosure to draw fluid from said tubes in the sample plate;

and said collection plate supported on means to move said collection plate vertically in said enclosure and adjacent said sample plate;

said vacuum means drawing samples from a bottom of said sample plate into said collection plate such that each sample in said sample plate is directed to a corresponding said vertical tube in said collection plate without cross talk between adjacent tubes whereby said collection plate has been moved vertically proximate to said sample plate.

* * * * *